United States Patent
Imahori et al.

(10) Patent No.: US 11,007,383 B2
(45) Date of Patent: May 18, 2021

(54) MEASUREMENT DEVICE AND MEASUREMENT PROBE

(71) Applicants: Cancer Intelligence Care Systems, Inc., Tokyo (JP); FUJIDENOLO CO., LTD., Komaki (JP)

(72) Inventors: Yoshio Imahori, Tokyo (JP); Tsuyako Takeyoshi, Tokyo (JP); Hideki Miyazaki, Komaki (JP); Shinsuke Kato, Komaki (JP); Norihide Takeuchi, Komaki (JP); Akari Sakuragi, Komaki (JP)

(73) Assignees: Cancer Intelligence Care Systems, Inc., Tokyo (JP); FUJIDENOLO CO., LTD., Komaki (JP)

( * ) Notice: Subject to any disclaimer, the term of this patent is extended or adjusted under 35 U.S.C. 154(b) by 0 days.

(21) Appl. No.: 16/534,035

(22) Filed: Aug. 7, 2019

(65) Prior Publication Data

US 2020/0001116 A1    Jan. 2, 2020

Related U.S. Application Data

(63) Continuation of application No. PCT/JP2017/007040, filed on Feb. 24, 2017.

(30) Foreign Application Priority Data

Feb. 9, 2017   (JP) .............................. JP2017-022623

(51) Int. Cl.
*A61N 5/00* (2006.01)
*A61N 5/10* (2006.01)
*A61K 41/00* (2020.01)

(52) U.S. Cl.
CPC ......... *A61N 5/1049* (2013.01); *A61N 5/1031* (2013.01); *A61N 5/1071* (2013.01);
(Continued)

(58) Field of Classification Search
USPC ...................................................... 250/491.1
See application file for complete search history.

(56) References Cited

U.S. PATENT DOCUMENTS

| 4,900,933 A | 2/1990 | Nestor |
| 5,708,739 A * | 1/1998 | Patton ................ G02B 6/02142 |
| | | 385/37 |

(Continued)

FOREIGN PATENT DOCUMENTS

| JP | H11-118933 A | 4/1999 |
| JP | 2008-89310 A | 4/2008 |

(Continued)

OTHER PUBLICATIONS

English translation of International Search Report of International Application No. PCT/JP2017/007040 dated May 23, 2017.

(Continued)

*Primary Examiner* — Phillip A Johnston
(74) *Attorney, Agent, or Firm* — Muncy, Geissler, Olds & Lowe, P.C.

(57) ABSTRACT

A measurement device includes a sensing portion and a measuring portion. The sensing portion contains at least a fluorescent material whose emitting of fluorescent light ceases due to an action of a radioactive beam. The measuring portion measures a radiation quantity of the radioactive beam, with which the sensing portion is irradiated, based on an amount of decrease in the intensity of the fluorescent light emitted by the fluorescent material contained in the sensing portion when the radioactive beam acts on at least a portion of the fluorescent material. The fluorescent light is emitted due to irradiation of the fluorescent material by an excitation source.

11 Claims, 12 Drawing Sheets

(52) U.S. Cl.
    CPC ........ *A61N 5/1077* (2013.01); *A61K 41/0095* (2013.01); *A61N 2005/109* (2013.01); *A61N 2005/1094* (2013.01); *A61N 2005/1095* (2013.01)

(56) References Cited

U.S. PATENT DOCUMENTS

| | | | |
|---|---|---|---|
| 8,993,968 B2 * | 3/2015 | Walker | G21K 4/00 |
| | | | 250/361 R |
| 9,182,349 B2 * | 11/2015 | Nitta | G01N 1/30 |
| 10,213,373 B2 * | 2/2019 | Loupis | A61N 5/0616 |
| 2003/0206320 A1 * | 11/2003 | Cole | G03H 1/02 |
| | | | 359/15 |
| 2004/0072278 A1 * | 4/2004 | Chou | G01N 15/1456 |
| | | | 435/29 |
| 2010/0176308 A1 | 7/2010 | Yu et al. | |
| 2012/0251453 A1 | 10/2012 | Fukuda | |
| 2013/0252340 A1 | 9/2013 | Haertling | |
| 2016/0200970 A1 | 7/2016 | Sakurai et al. | |

FOREIGN PATENT DOCUMENTS

| | | | |
|---|---|---|---|
| JP | 2016104871 A | 6/2016 | |
| JP | 2016-529477 A | 9/2016 | |

OTHER PUBLICATIONS

Office action for the corresponding JP application No. 2018-566737 dated Oct. 20, 2020 and English translation thereof.
Extended European search report of the corresponding EP application No. 17895823.7 dated Nov. 6, 2020.

* cited by examiner

FIG. 4

| | |
|---|---|
| (a) 1,3,5,7-Tetramethyl-8-phenyl-4,4-difluoroboradiazaindacene 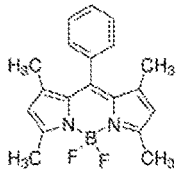 | (d) {3-Ethyl-5-[(4-ethyl-3,5-dimethyl-2H-pyrrol-2-ylidene)methyl]-2,4-dimethyl-1H-pyrrolato-N1,N5}difluoroboron 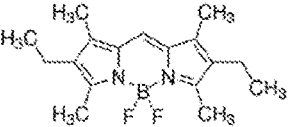 |
| (b) 2,6-Diethyl-4,4-difluoro-1,3,5,7-tetramethyl-8-[4-(2-propinyloxy)phenyl]-4-bora-3a,4a-diaza-s-indacene 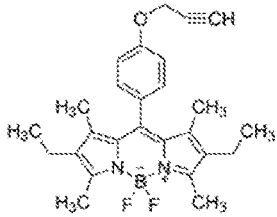 | (e) 8-[4-(2-Azidoethoxy)phenyl]-2,6-diethyl-4,4-difluoro-1,3,5,7-tetramethyl-3a,4a-diaza-4-bora-s-indacene 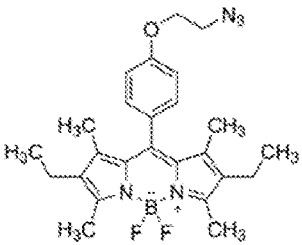 |
| (c) 2,8-Diethyl-1,3,5,7-tetramethyl-9-phenylbipyrromethene difluoroborate 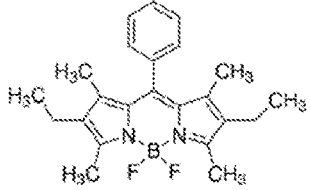 | (f) Difluoro{2-[1-(3,5-dimethyl-2H-pyrrol-2-ylidene-N)ethyl]-3,5-dimethyl-1H-pyrrolato-N}boron 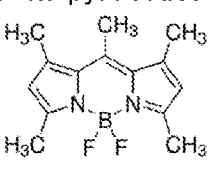 | ized by a photoelectric converter and is measured. The amount of the radiation is thus specified.

MEASUREMENT DEVICE AND MEASUREMENT PROBE

CROSS-REFERENCE TO RELATED APPLICATION

This application is a Continuation Application of International Application No. PCT/JP2017/007040, filed Feb. 24, 2017, which claims priority from Japanese Patent Application No. 2017-022623, filed on Feb. 9, 2017. This disclosure of the foregoing application is hereby incorporated by reference in its entirety.

BACKGROUND

The present disclosure relates to a measurement device and a measurement probe for measuring an amount of radiation.

A measurement device that uses a scintillator is known as a device that is able to measure an amount of radiation. The measurement device discloses a fiber-type radiation detection device. The fiber-type radiation detection device has a structure in which a fluorescent optical fiber has been inserted into a central portion of an acrylic resin member with high optical transparency. A radiation sensing layer containing a scintillator is formed on the outer circumferential surface of the acrylic resin member. In a case where radiation is incident to the radiation sensing layer, the scintillator absorbs the radiation, causing it to emit a fluorescent light (called a first fluorescent light). The first fluorescent light passes through the acrylic resin member and is absorbed by the fluorescent optical fiber. The fluorescent optical fiber then emits a fluorescent light (called a second fluorescent light) having a different wavelength from that of the first fluorescent light. As the second fluorescent light advances through the core of the fluorescent optical fiber, it is converted into an electrical signal by a photoelectric converter and is measured. The amount of the radiation is thus specified.

SUMMARY

In the detection device described above, the amount of the radiation is measured by measuring the fluorescent light emitted by the incidence of the radiation to the scintillator. However, because the amount of the light that is emitted by the scintillator is minuscule, a photomultiplier tube or an extremely high-sensitivity measuring device is required in order to measure the light. Therefore, a problem arises in that the device becomes complex and expensive.

An object of the present disclosure is to provide a measurement device and a measurement probe that are capable of measuring an amount of radiation with high sensitivity.

Various embodiments herein provide a measurement device including a sensing portion and a measuring portion. The sensing portion contains at least a fluorescent material whose emitting of fluorescent light ceases due to an action of a radioactive beam. The measuring portion measures a radiation quantity of the radioactive beam, with which the sensing portion is irradiated, based on an amount of decrease in the intensity of the fluorescent light emitted by the fluorescent material contained in the sensing portion when the radioactive beam acts on at least a portion of the fluorescent material. The fluorescent light is emitted due to irradiation of the fluorescent material by an excitation source.

Embodiments also provide a measurement probe used in a measurement device configured to measure a radiation quantity of a radioactive beam. The measurement probe includes a sensing portion and a transmitting portion. The sensing portion contains at least a fluorescent material whose emitting of fluorescent light ceases due to an action of the radioactive beam. The transmitting portion is connected to the sensing portion and configured to transmit the fluorescent light being emitted due to irradiation of the fluorescent material by an excitation source.

BRIEF DESCRIPTION OF DRAWINGS

Embodiments will be described below in detail with reference to the accompanying drawings in which:

FIG. 4 is a figure showing examples of BODIPY compounds that are fluorescent materials containing boron.

DETAILED DESCRIPTION

Figure 1:
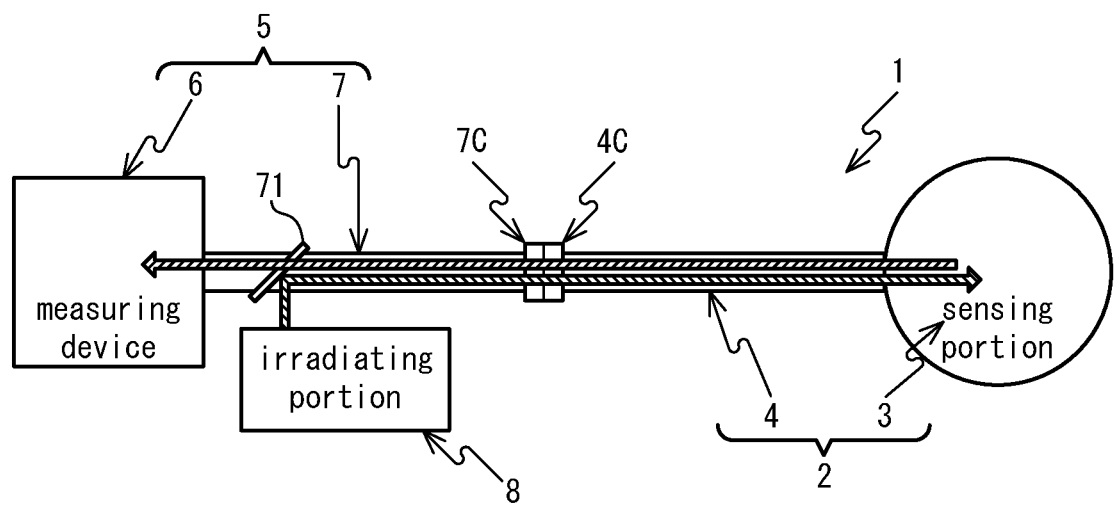
FIG. 1 is a figure showing an overview of a measurement device 1.

A measurement device 1 according to an embodiment of the present disclosure will be explained with reference to the drawings. The measurement device 1 is a device that is capable of measuring neutron fluence. As shown in FIG. 1, the measurement device 1 includes a measurement probe 2, a measuring portion 5, and an irradiating portion 8.

Measurement Probe 2

The measurement probe 2 is detachably connected to the measuring portion 5. The measurement probe 2 includes a sensing portion 3 and a first transmitting portion 4. The sensing portion 3 is formed by using one of mixing, enclosing, and coating to combine a fluorescent material with one of transparent resin and glass. The amount of the fluorescent material that is mixed into the one of transparent resin and glass is not explicitly specified, but the amount that is mixed in may be several parts per million by weight, for example. The form of the sensing portion 3 is shown schematically in FIG. 1. The form of the sensing portion 3 will be explained later. The first transmitting portion 4 is an optical fiber, and connected to a portion of the sensing portion 3. Polyester, polycarbonate, polystyrene, polyvinyl chloride, acrylic resin, epoxy resin, and the like can be used as the material of the transparent resin. Note that the transparent resin is not limited to the specific examples above, and another resin having transparency can also be used.

A distinctive property of the fluorescent material is that when a neutron beam acts on it, the material stops emitting fluorescent light. The material that is used as the fluorescent material includes at least one of hydrogen (H), lithium (Li), boron (B), cadmium (Cd), gadolinium (Gd), samarium (Sm), europium (Eu), and dysprosium (Dy), for example, which are elements with large neutron capture cross sections. Of these, a material that includes lithium (Li), boron (B), and gadolinium (Gd) is preferable. Note that the fluorescent material may have a molecular structure including at least one of the plurality of elements listed above, and it may be formed by using doping to cause at least one of the plurality of elements listed above to be incorporated.

Figure 2:
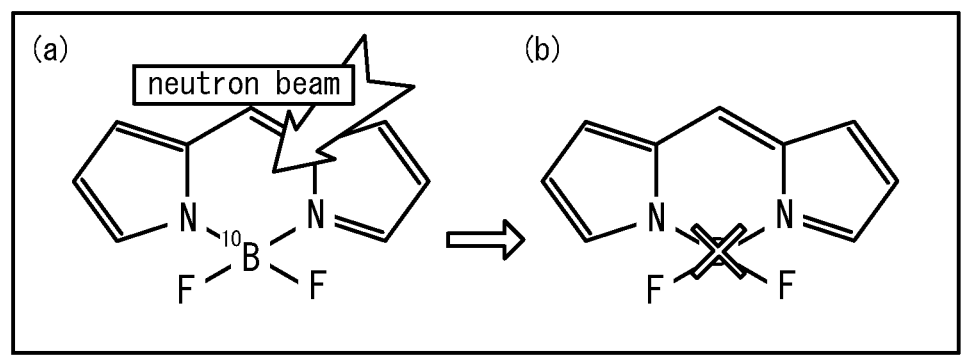
FIG. 2 is a figure showing a change that occurs when a neutron beam acts on a BODIPY compound.

FIG. 2 shows a change in molecular structure that occurs when a neutron beam acts on a BODIPY (boron-dipyrromethene) compound, which is an example of the fluorescent material. BODIPY compounds are known fluorescent dyes, and they emit fluorescent light in response to being irradiated with excitation light. BODIPY compounds contain boron in their molecular structure. Naturally occurring boron is ordinarily a mixture in which the isotope $^{11}B$ constitutes approximately 80% and the isotope $^{10}B$ constitutes approximately 20%, but the neutron capture cross section of the isotope $^{10}B$ is extremely large. Therefore, in a case where a BODIPY compound is irradiated with a neutron beam, as shown in FIG. 2(a), the boron absorbs the neutron beam, and the atomic nucleus of the boron is destroyed. The BODIPY compound thus ceases to be fluorescent. In this state, fluorescent light is not emitted, even if the BODIPY compound is irradiated with excitation light.

Figure 3:
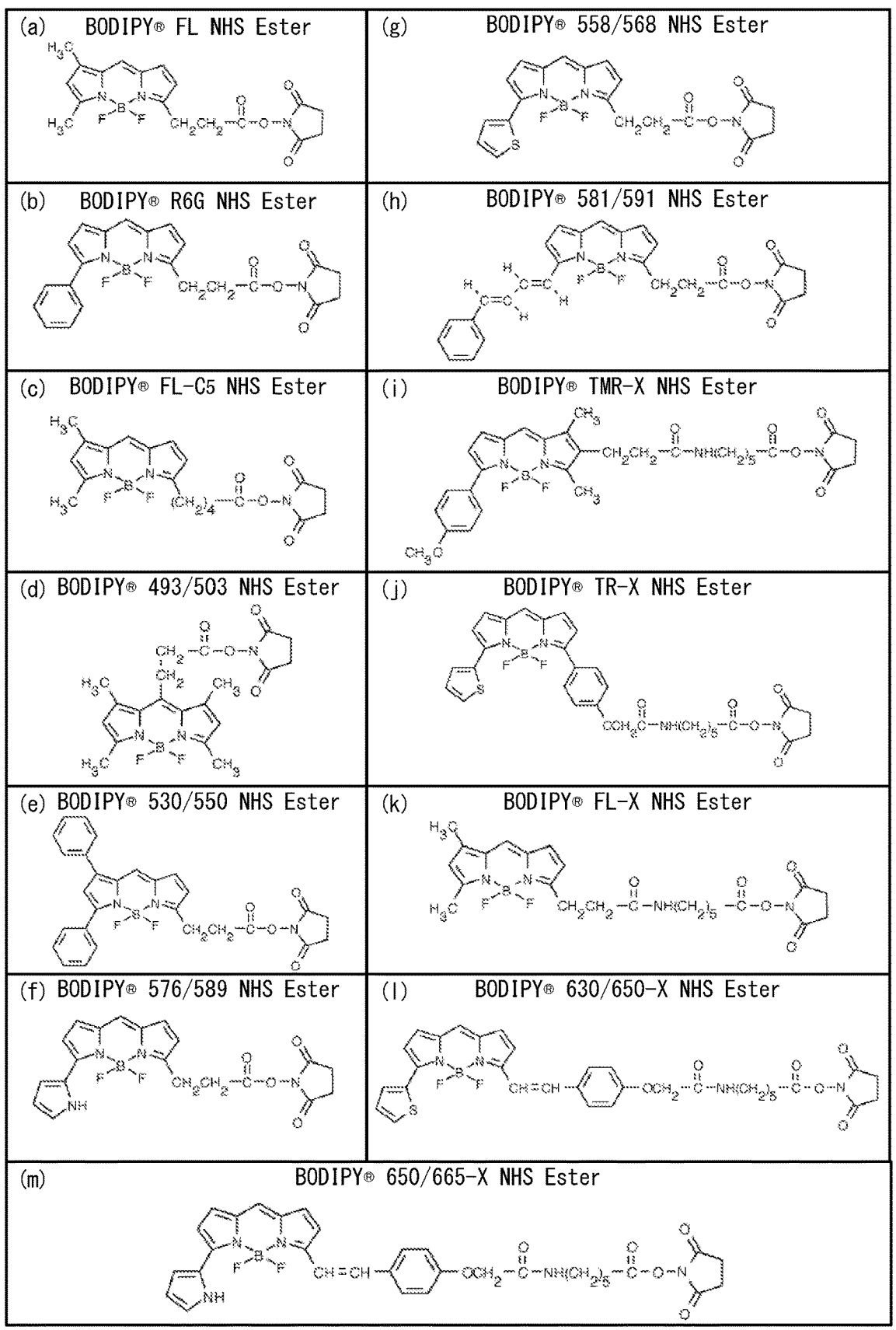
FIG. 3 is a figure showing examples of BODIPY compounds that are fluorescent materials containing boron.

Various types of BODIPY compounds made by Thermo Fisher Scientific, such as those shown in FIGS. 3(a) to 3(m), for example, can be used as the BODIPY compound. Various types of BODIPY compounds made by Sigma-Aldrich, such as those shown in FIGS. 4(a) to 4(f), for example, can also be used. Note that the compound names in FIG. 3 and FIG. 4 are the product names used at the respective companies. A different fluorescent material that also contains boron and can be used is a complex of chromotropic acid and boric acid. The precision of neutron beam measurement can also be improved by manufacturing and using a fluorescent material in which the ratio of the isotope $^{10}B$ has been deliberately increased.

Lucifer Yellow CH dilithium salt and the like made by Sigma-Aldrich can also be used as fluorescent materials that contain lithium. Type: QUMK58/F-D1 (yttrium gadolinium aluminum oxide: cerium, $(Y, Gd)_3Al_5O_{12}:Ce$) and Type: UKL63/F-U1 (gadolinium oxysulfide: europium, $Gd_2O_2S$: Eu), made by U-VIX, can also be used as fluorescent materials that contain gadolinium. $Gd_2O_2S$:Tb, made by U-VIX, as well as $(Y, Gd)BO_3$:Eu, $(Y, Gd)_2O_3$:Eu, and the like, made by Nemoto & Co., Ltd., can also be used.

Figure 5:
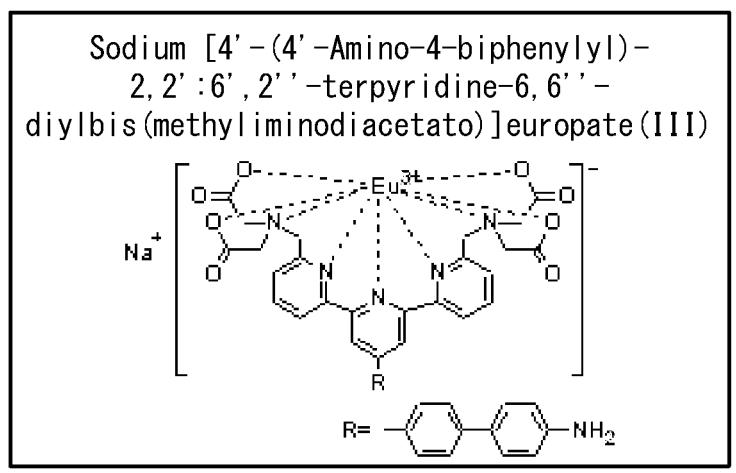
FIG. 5 is a figure showing an example of a fluorescent material containing europium.

Type: KEMK63M/F-U1 (barium magnesium aluminate: europium, manganese, $BaMg_2Al_{16}O_{27}$: Eu,Mn), Type: HL63/S-D1 (strontium sulfide: europium, SrS:Eu), Type: FL63/S-D1 (calcium sulfide: europium, CaS:Eu), Type: KEMK63/F-P1 (barium magnesium aluminate: europium, $BaMg_2Al_{16}O_{27}$: Eu), Type: UKL63/F-U1 (gadolinium oxysulfide: europium, $Gd_2O_2S$:Eu), and Type: HPL63/F-F1 (strontium thiogallate: europium, $SrGa_2S_4$:Eu), made by U-VIX, can also be used as fluorescent materials that contain europium. The material shown in FIG. 5, made by Tokyo Chemical Industry Co. Ltd., can also be used. $(Ba,Sr)MgAl_{10}O_{17}$: Eu, $Y_2O_3$: Eu, $BaMgAl_{10}O_{17}$: Eu, $(Y, Gd)BO_3$: Eu, $Y(P,V)O_4$: Eu, $(Y, Gd)_2O_3$: Eu, $Sr_5(PO_4)_3Cl$: Eu, $Y_2O_2S$: Eu, and $La_2O_2S$: Eu, made by Nemoto & Co., Ltd., can also be used.

Note that the materials cited above are merely examples, and the fluorescent material is not limited to these examples. Various types of organic and inorganic materials can be used as the fluorescent material, as long as they are materials that have the property that they cease emitting fluorescent light when a neutron beam acts on them. The fluorescent material may also be any one of a liquid, a gas, and a solid.

Figure 6:
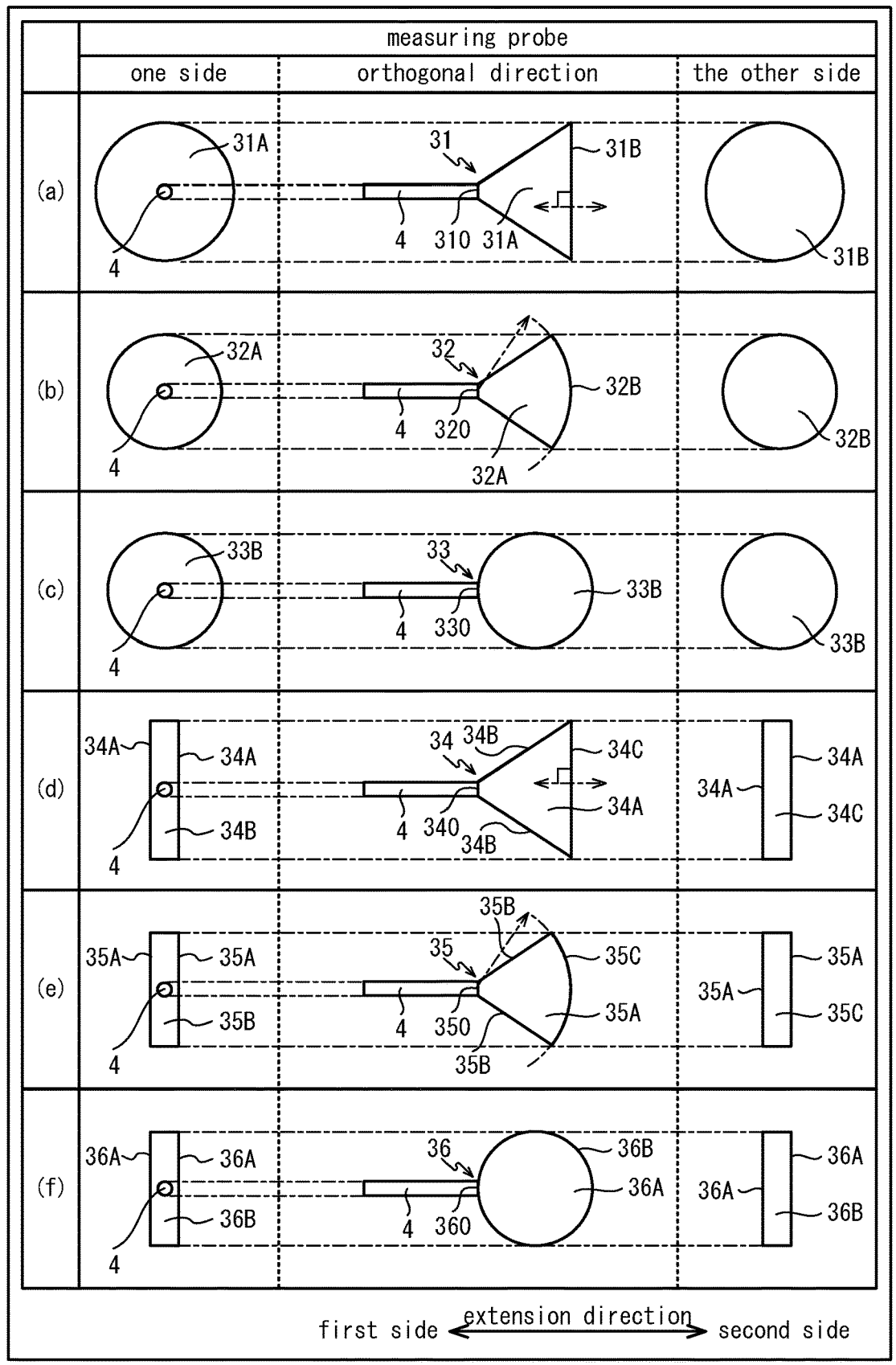
FIG. 6 is a figure showing various shapes of a sensing portion 3 of a measurement probe 2.

Variously shaped sensing portions 31 to 36, shown in FIG. 6, for example, can be used as the sensing portion 3. Hereinafter, the various sensing portions 31 to 36 will be explained. Note that the shape of the sensing portion 3 reflects the shape of the one of the transparent resin and the glass in which the sensing portion 3 is contained.

As shown in FIG. 6(a), the shape of the sensing portion 31 is a cone with a flat bottom face. In the sensing portion 31, a first end of the first transmitting portion 4 is connected to a position 310, which corresponds to the apex of the cone. The direction in which the first transmitting portion 4 extends from the position 310 of the sensing portion 31 is called the extension direction. In other words, of the directions in which the first transmitting portion 4 extends, the extension direction is the direction starting from the portion where the first transmitting portion 4 is connected to the sensing portion 31. In the extension direction, the side where the first transmitting portion 4 is disposed at the position 310 is called the first side, and the side where the sensing portion 31 is disposed at the position 310 is called the second side. FIG. 6 shows the shape of the sensing portion 31 as seen from the first side in the extension direction, from the second side in the extension direction, and from a direction (called the orthogonal direction) that is orthogonal to the extension direction. Note that the definitions of the directions described above also apply to the sensing portions 32 to 36, which are described below.

Figure 7:
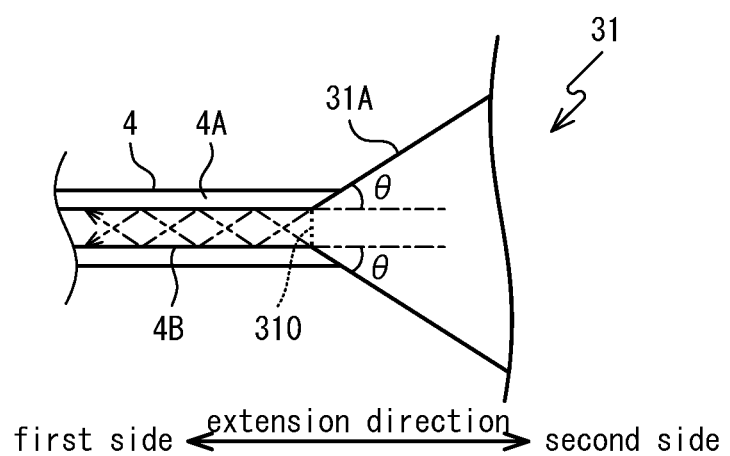
FIG. 7 is an enlarged view of a portion connecting a sensing portion 31 and a first transmitting portion 4.

On the outer surface of the sensing portion 31, the portion corresponding to the side face of the cone is called the radiating portion 31A, and the portion corresponding to the bottom face of the cone is called the flat portion 31B. The radiating portion 31A extends radiating outward toward the flat portion 31B from the position 310, which is connected to the first end of the first transmitting portion 4. As shown in FIG. 7, an angle θ that is formed between the extension direction and the direction extending along the radiating portion 31A from the position 310 toward the flat portion 31B is defined such that its relationship to the numerical aperture NA of the first transmitting portion 4 is described by the following equation:

$$NA = \sin \theta$$

That is, the angle of the radiating portion 31A in relation to the extension direction is congruent with the maximum incidence angle of the light coming into the first end of the first transmitting portion 4, which is the maximum light-receiving angle of the first transmitting portion 4. The angle θ may be 30 degrees, for example. As shown in FIG. 6(a), the flat portion 31B has a flat shape corresponding to the end portion of the sensing portion 31 on the second side in the extension direction. The flat portion 31B is orthogonal to the extension direction.

As shown in FIG. 6(b), the shape of the sensing portion 32 differs from that of the sensing portion 31 in that its bottom face is spherical. A radiating portion 32A and a position 320, to which the first end of the first transmitting portion 4 is connected, respectively correspond to the radiating portion 31A and the position 310 of the sensing portion 31. On the outer surface of the sensing portion 32, the portion corresponding to the bottom face of the cone is called the spherical surface portion 32B. The spherical surface portion 32B corresponds to the end portion of the sensing portion 32 on the second side in the extension direction, and it is disposed along the surface of a virtual sphere having its center at the position 320.

As shown in FIG. 6(c), the shape of the sensing portion 33 is spherical. The outer surface of the sensing portion 33 is called the spherical portion 33B. The first end of the first transmitting portion 4 is connected to a position 330 on the spherical portion 33B.

As shown in FIG. 6(d), the shape of the sensing portion 34 is a triangular plate shape. The outer surfaces of the sensing portion 34 include a pair of main face portions 34A, a pair of radiating portions 34B, and a flat portion 34C, each of which is flat. The pair of the main face portions 34A are each triangular. The pair of the main face portions 34A are disposed parallel to one another, with a specified gap between them. The pair of the radiating portions 34B each extend along the entire length of two parallel edges of the pair of the main face portions 34A. The pair of the radiating portions 34B are connected at a position corresponding to the apex of one of the pair of the main face portions 34A. The first end of the first transmitting portion 4 is connected to a position 340, to which each one of the pair of the radiating portions 34B is connected. The flat portion 34C corresponds to the end portion of the sensing portion 34 on the second side in the extension direction. The flat portion 34C has a flat shape. The flat portion 34C extends between the pair of the main face portions 34A, on the side of the pair of the main face portions 34A to which the pair of the radiating portions 34B are not connected.

Each of the radiating portions 34B extends radiating outward toward the flat portion 34C from the position 340, to which the first transmitting portion 4 is connected. An angle θ that is formed between the extension direction and the direction extending along each of the radiating portions 34B from the position 340 toward the flat portion 34C is congruent with the maximum light-receiving angle of the first transmitting portion 4 (refer to FIG. 7). The flat portion 34C is orthogonal to the extension direction.

As shown in FIG. 6(e), the shape of the sensing portion 35 is a fan-shaped plate shape. The outer surfaces of the sensing portion 35 include a pair of main face portions 35A and a pair of radiating portions 35B, each of which is flat, as well as a curved portion 35C. The pair of the main face portions 35A are each fan-shaped. The pair of the main face portions 35A are disposed parallel to one another, with a specified gap between them. The pair of the radiating portions 35B each extend along the entire length of two parallel radial edges of the pair of the main face portions 35A. The pair of the radiating portions 35B are connected at a position corresponding to the position where the two radial edges of the pair of the main face portions 34A intersect. The first end of the first transmitting portion 4 is connected to a position 350, to which each one of the pair of the radiating portions 35B is connected. The curved portion 35C extends along and between parallel arc-shaped edges of the pair of the main face portions 34A. The curved portion 35C is curved.

Each of the radiating portions 35B extends radiating outward toward the curved portion 35C from the position 350, to which the first transmitting portion 4 is connected. An angle θ that is formed between the extension direction and the direction extending along each of the radiating portions 35B from the position 350 toward the curved portion 35C is congruent with the maximum light-receiving angle of the first transmitting portion 4 (refer to FIG. 7). The curved portion 35C is disposed along the side face of a virtual cylinder whose central axis passes through the position 350 and is orthogonal to the pair of the main face portions 35A.

As shown in FIG. 6(f), the shape of the sensing portion 36 is a circular plate shape. The outer surfaces of the sensing portion 36 include a pair of main face portions 36A, each of which is flat, and a side face portion 36B. The pair of the main face portions 36A are each circular. The pair of the main face portions 36A are disposed parallel to one another, with a specified gap between them. The side face portion 36B extends around the circumference of the pair of the main face portions 35A, spanning the gap between them. The side face portion 36B is curved. The first end of the first transmitting portion 4 is connected to a position 360 on the side face portion 36B.

A reflective member that is not shown in the drawings is connected to each one of the flat portion 31B of the sensing portion 31 (refer to FIG. 6(a)), the spherical surface portion 32B of the sensing portion 32 (refer to FIG. 6(b)), and the spherical portion 33B of the sensing portion 33 (refer to FIG. 6(c)) between the center and the second side in the extension direction, and is connected to each one of the flat portion 34C of the sensing portion 34 (refer to FIG. 6(d)), the curved portion 35C of the sensing portion 35 (refer to FIG. 6(e)), and the side face portion 36B of the sensing portion 36 (refer to FIG. 6(f)) between the center and the second side in the extension direction. The reflective member is in the form of a film. The reflective member is affixed to the sensing portion 3 in a state in which a reflective surface with a high reflection ratio is placed close to and facing the sensing portion 3 side. The reflective member causes light that travels from the sensing portion 3 toward the outside to be reflected to the inner side of the sensing portion 3. The sensing portion 3 and a reflective plate are also covered by a light shielding member that is not shown in the drawings. The light shielding member prevents outside light from entering the sensing portion 3. Note that at least one of the reflective member and the light shielding member may also be omitted from the sensing portion 3. The sensing portion 3 may also be covered with an acrylic resin or the like on the outer side of the light shielding member.

As shown in FIG. 7, the first transmitting portion 4 includes a cladding 4A and a core 4B. The core 4B is made of an acrylic resin. As shown in FIG. 1, the first end of the first transmitting portion 4 is connected to the sensing portion 3. A joint 4C is connected to a second end of the first transmitting portion 4. The joint 4C can be connected to a joint 7C of a second transmitting portion 7, which will be described later. The first transmitting portion 4 forms a connection between the sensing portion 3 and the measuring portion 5, which will be described below.

Measuring Portion 5

As shown in FIG. 1, the measuring portion 5 includes a measuring device 6 and the second transmitting portion 7. The measuring device 6 is a spectrophotometer. The measuring device 6 measures, at each individual frequency, the intensity of light that is transmitted through the second transmitting portion 7, which is described below. The second transmitting portion 7 is an optical fiber. The second transmitting portion 7 includes a cladding and a core, which are not shown in the drawings. The core of the second transmitting portion 7 is made of quartz. One end of the second transmitting portion 7 is connected to the measuring device 6. The other end of the second transmitting portion 7 is connected to the joint 7C. The joint 7C can be connected to the joint 4C of the first transmitting portion 4 of the measurement probe 2.

Note that one of a dichroic filter and a longpass filter may be interposed at the point where the measuring device 6 and the second transmitting portion 7 are connected. The measuring device 6 may also be a photometer that measures the intensity of light at a specified frequency. It is preferable for the measuring portion 5 to be resistant to neutron beams, in order to suppress the influence of neutron beams entering from outside. It is also preferable for the measuring portion 5 to be resistant to excitation light, in order to suppress the influence of excitation light emitted by the irradiating portion 8, which will be described below. For example, the measuring device 6 may be installed inside a shielding member that is capable of shielding it from neutron beams and excitation light.

Irradiating Portion 8

The irradiating portion 8 outputs excitation light for the purpose of causing fluorescent light to be emitted from the fluorescent material of the sensing portion 3. The excitation light is emitted toward a dichroic mirror 71 that is provided in a portion of the second transmitting portion 7 of the measuring portion 5. From the excitation light, the dichroic mirror 71 selectively reflects light of a wavelength that is able to cause fluorescent light to be emitted from the fluorescent material, while allowing light of other wavelengths to pass through.

Method for Measuring Neutron Fluence

Figure 8:
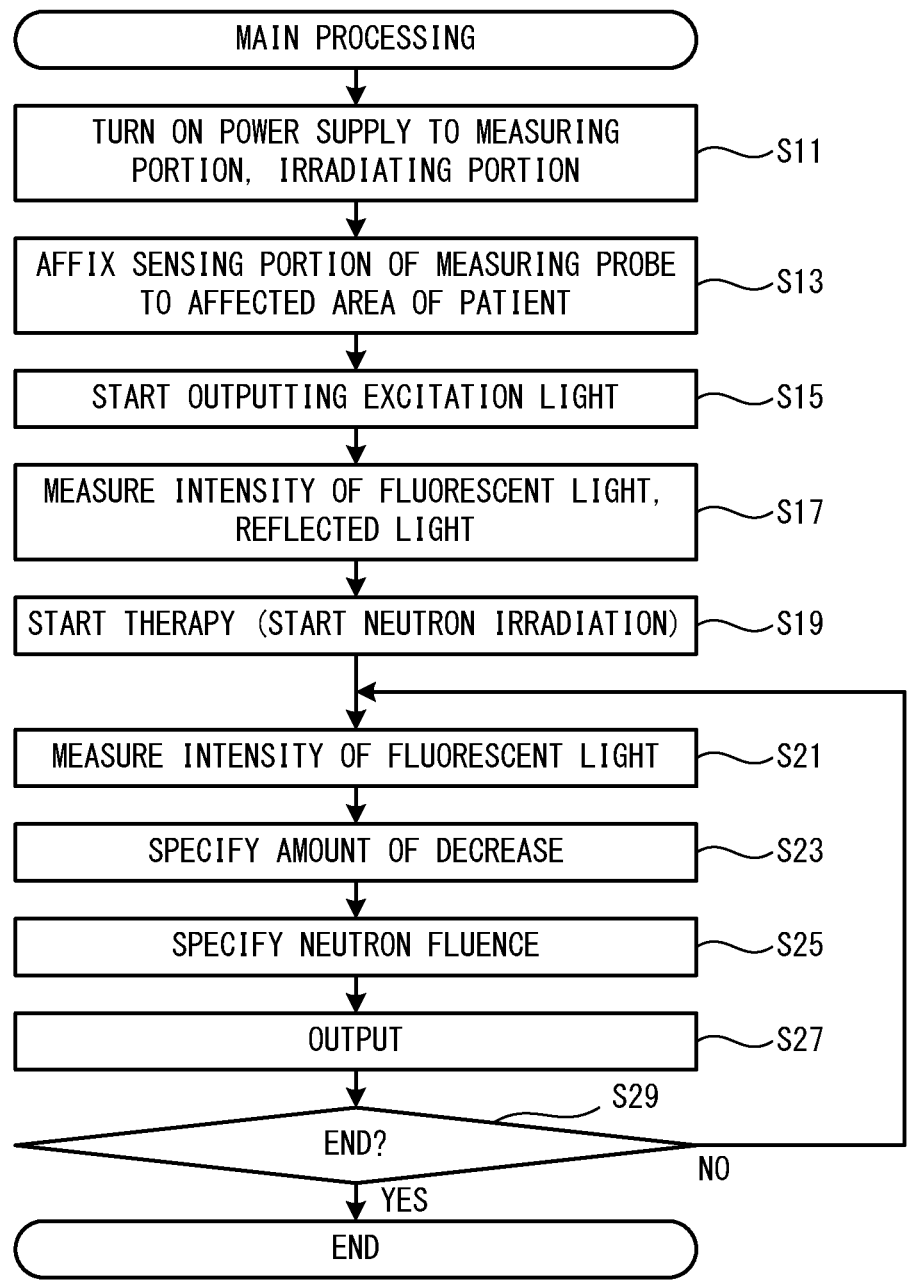
FIG. 8 is a flowchart showing a method for measuring neutron fluence using the measurement device 1.

A method that is used by the measurement device 1 for measuring neutron fluence will be explained with reference to FIG. 8. The uses of the measurement device 1 are not specifically limited, but the measurement device 1 may be used in neutron capture therapy, for example, for measuring the neutron fluence of a neutron beam with which a patient is irradiated. The explanation that follows assumes a case in which the measurement device 1 is used for this purpose.

First, the joint 4C of the first transmitting portion 4 of the measurement probe 2 is connected to the joint 7C of the second transmitting portion 7 of the measuring portion 5. Note that the measurement probe 2 is replaced every time that measuring is performed. The power supply to the irradiating portion 8 and the measuring device 6 of the measuring portion 5 is turned on (Step S11). The sensing portion 3 of the measurement probe 2 is affixed to one of an affected area and a surface of a patient who is to be treated by neutron capture therapy (Step S13). The output of excitation light from the irradiating portion 8 is started (Step S15). Note that at this point, the irradiating of the affected area of the patient by the neutron beam has not been started.

As shown in FIG. 1, the excitation light that is output from the irradiating portion 8 arrives at the dichroic mirror 71. From the excitation light, the dichroic mirror 71 selectively reflects light of a wavelength (for example, 400 to 500 nm) that is able to cause fluorescent light to be emitted from the fluorescent material of the sensing portion 3. The excitation light that is reflected by the dichroic mirror 71 is transmitted through the second transmitting portion 7 to the first transmitting portion 4. The excitation light travels to the first transmitting portion 4 through the joints 7C, 4C and is further transmitted through the first transmitting portion 4 to the sensing portion 3. The excitation light enters the sensing portion 3 from the first end of the first transmitting portion 4.

The excitation light that has traveled to the sensing portion 3 irradiates the fluorescent material of the sensing portion 3. Being irradiated by the excitation light, the fluorescent material emits fluorescent light. The fluorescent light that is emitted from the fluorescent material travels through the sensing portion 3 toward the first transmitting portion 4 and enters the first transmitting portion 4. The fluorescent light is also reflected by the reflective member that is provided on the surface of the sensing portion 3. The reflected fluorescent light travels through the sensing portion 3 toward the first transmitting portion 4 and enters the first transmitting portion 4. The excitation light that has entered the sensing portion 3 is also reflected by the reflective member. The reflected excitation light (called the reflected light) travels through the sensing portion 3 toward the first transmitting portion 4 and enters the first transmitting portion 4.

The fluorescent light and the reflected light that have entered the first transmitting portion 4 are transmitted through the first transmitting portion 4 to the second transmitting portion 7. The fluorescent light and the reflected light enter the second transmitting portion 7 through the joints 4C, 7C and are transmitted through the second transmitting portion 7 to the measuring device 6. The fluorescent light and the reflected light pass through the dichroic mirror 71 and arrive at the measuring device 6. The measuring device 6 detects the fluorescent light and the reflected light. As shown in FIG. 8, the measuring device 6 separates out the light at the wavelength of the fluorescent light (for example, 500 to 600 nm) and then measures the intensity of the fluorescent light (Step S17). The measuring device 6 separates out the light at the wavelength of the reflected light (for example, 400 to 500 nm) and then measures the intensity of the reflected light (Step S17).

The therapy is started by starting the irradiation of the affected area of the patient by a neutron beam (Step S19). Because the neutron beam also irradiates the sensing portion 3 that is affixed to the affected area of the patient, the neutron beam acts on at least a portion of the fluorescent material of the sensing portion 3. In the fluorescent material on which the neutron beam has acted, the emitting of the fluorescent light ceases. Therefore, the intensity of the fluorescent light that is emitted from the fluorescent material as a whole decreases from what it was before the irradiating by the neutron beam was started.

After the irradiating by the neutron beam has started, the measuring device 6 separates out the light at the wavelength of the fluorescent light and measures the intensity of the fluorescent light (Step S21). The measuring device 6 specifies the amount of the decrease in the intensity of the fluorescent light by subtracting the intensity of the fluorescent light that was measured at Step S21, that is, the intensity of the fluorescent light after the irradiating by the neutron beam, from the intensity of the fluorescent light that was measured at Step 17, that is, the intensity of the fluorescent light before the irradiating by the neutron beam, or by computing the ratio of the two intensities (Step S23). Based on the specified amount of the decrease, the measuring device 6 specifies the neutron fluence of the neutron beam that irradiated the sensing portion 3 (Step S25).

The method for specifying the neutron fluence will be explained in detail. The greater the intensity of the excitation light that the irradiating portion 8 outputs, the greater the intensity of the fluorescent light that is emitted from the fluorescent material of the sensing portion 3 becomes. Further, the greater the neutron fluence of the neutron beam that irradiates the sensing portion 3, the greater the amount of the fluorescent material that ceases to emit fluorescent light becomes, so the greater the amount of the decrease computed at Step S23 becomes. For every intensity level of the reflected light, the relationship between the amount of the decrease and the neutron fluence of the neutron beam that irradiates the sensing portion 3 is stored in the measuring device 6 in advance. The measuring device 6 thus takes the neutron fluence that corresponds to the intensity of the reflected light that was measured at Step S17 and the amount of the decrease that was computed at Step S25 and specifies that as the neutron fluence of the neutron beam that irradiated the sensing portion 3.

The measuring device 6 outputs the specified neutron fluence to an output portion (a display portion or the like) that is not shown in the drawings (Step S27). In a case where a command to terminate measuring has not been input through an input portion (a switch or the like) that is not shown in the drawings (NO at Step S29), the measuring device 6 repeats the processing at Steps S21 to S27. In a state in which the sensing portion 3 is being irradiated by the neutron beam, the measuring device 6 cyclically repeats the specifying of the neutron fluence. In a case where a command to terminate measuring has been input (YES at Step S29), the measuring device 6 terminates the measuring of the neutron fluence.

Examples of Experiments

In a case where the sensing portion 3 of the measurement probe 2 was in a state in which it was not being irradiated by the neutron beam, the intensity of light detected by the measuring device 6 was actually measured. A first experiment was conducted using a version of the measurement probe 2 in which the sensing portion 3 contains a BODIPY compound as the fluorescent material and a version of the measurement probe 2 in which the sensing portion 3 does not contain the fluorescent material. The intensity of the light was measured by the measuring device 6 with the intensity of the excitation light output by the irradiating portion 8 being constant. In contrast, a second experiment was conducted using the measurement probe 2 in which the sensing portion 3 contains a BODIPY compound as the fluorescent material. The intensity of the light was measured by the measuring device 6 with the intensity of the excitation light output by the irradiating portion 8 being varied among four different levels.

Note that an epoxy resin was used as the transparent resin for the sensing portion 3 of the measurement probe 2. Where the BODIPY compound was used as the fluorescent material, the content was several parts per million in relation to the transparent resin. A Qmini spectrometer made by Opto Science, Inc., with on-board processing and evaluation for mobile applications, was used as the measuring device 6. An LED light source was used as the excitation light that is output from the irradiating portion 8. The results of the first experiment are shown in FIG. 9, and the results of the second experiment are shown in FIGS. 10 and 11.

Figure 9:
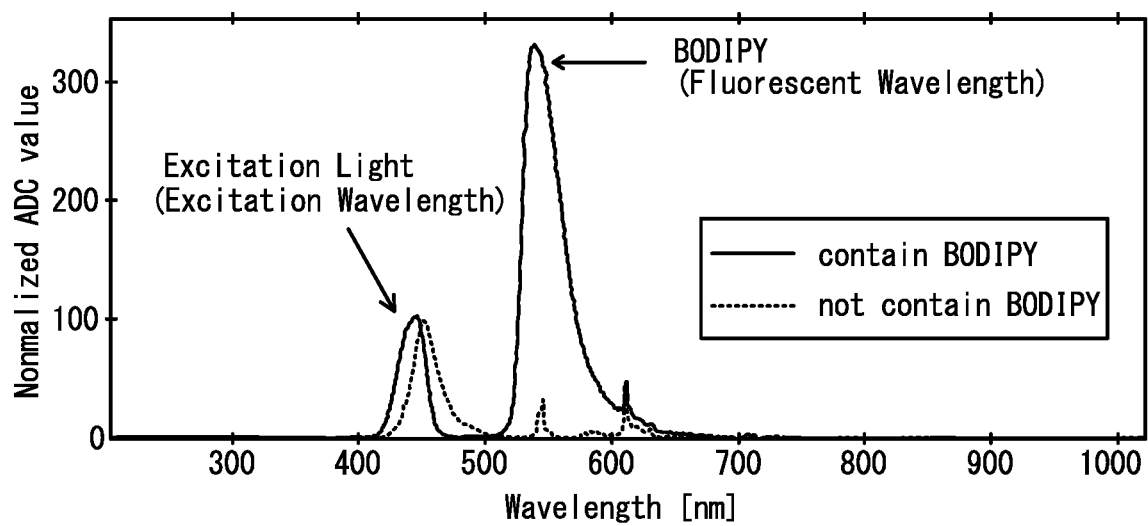
FIG. 9 is a graph showing results of an experiment 1.

In the first experiment, as shown in FIG. 9, when the measurement probe 2 that had the sensing portion 3 that does not contain the fluorescent material (the BODIPY compound) was used (the broken line in the graph), a peak attributable to the wavelength of the excitation light (the excitation wavelength) appeared at approximately 450 nm. In contrast, when the measurement probe 2 that had the sensing portion 3 that contains a BODIPY compound as the fluorescent material was used (the solid line in the graph), in addition to the approximately 450 nm peak attributable to the excitation wavelength, a peak attributable to the wavelength of the fluorescent light (the fluorescent wavelength) appeared at approximately 550 nm. These results make it clear that irradiating the sensing portion 3 with an excitation light for which the light source has a peak at approximately 450 nm causes fluorescent light that has a peak at approximately 550 nm to be emitted from the BODIPY compound.

Figure 10:
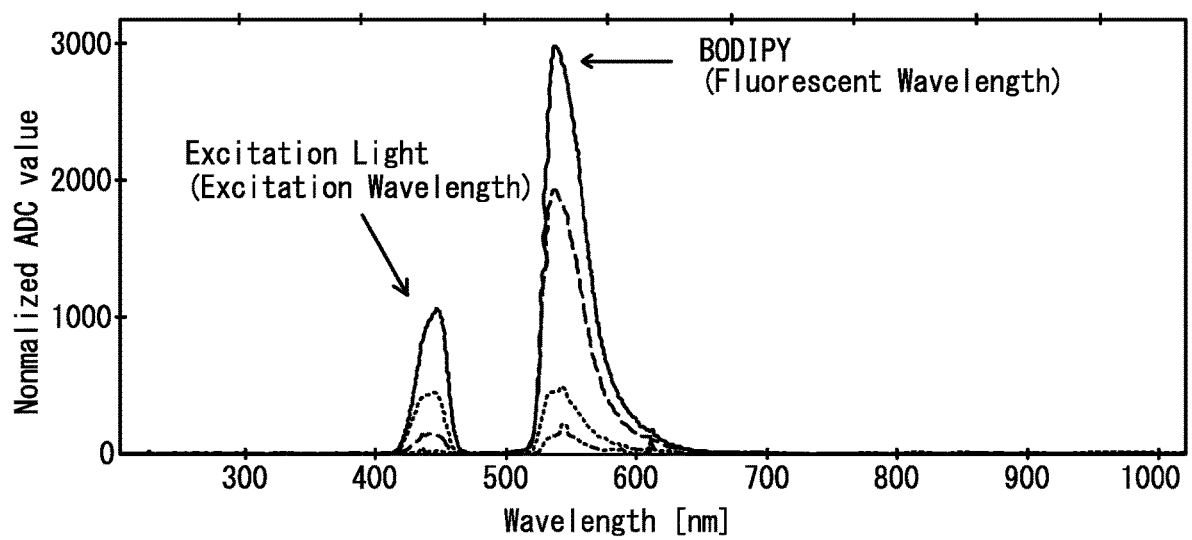
FIG. 10 is a graph showing results of an experiment 2.
Figure 11:
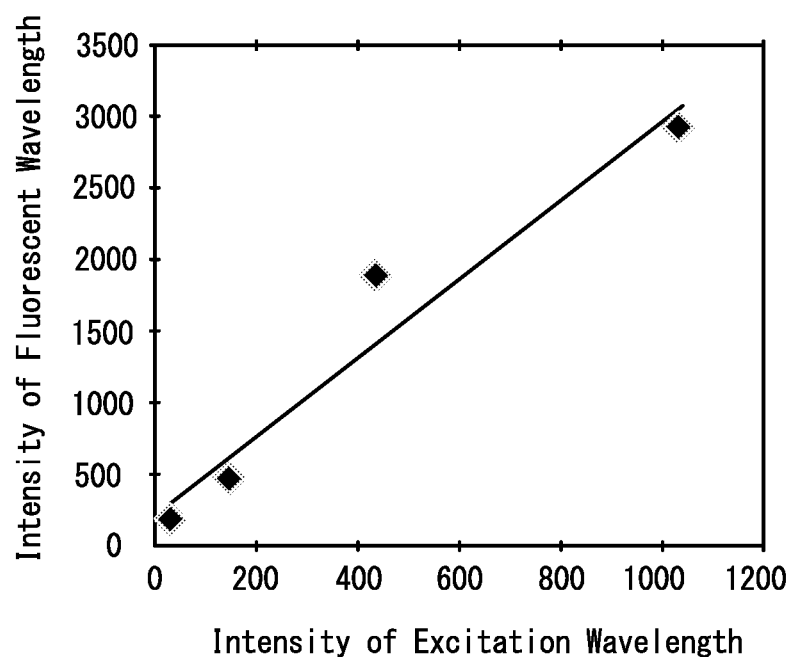
FIG. 11 is a graph showing results of the experiment 2.

In the second experiment, as shown in FIG. 10, it was shown that the intensity of the approximately 550 nm peak that corresponds to the fluorescent wavelength becomes greater as the intensity of the approximately 450 nm peak that corresponds to the excitation wavelength becomes greater. Based on these results, it is understood that the greater the intensity of the excitation light, the greater the intensity of the fluorescent light that is emitted from the fluorescent material becomes. As shown in FIG. 11, it was also shown that the intensity of the excitation light and the intensity of the fluorescent light wavelength have a more or less linear relationship. These results make it clear that the measurement device 1 is able to measure the intensity of the fluorescent light with good precision, without being dependent on the intensity of the excitation light that is output from the irradiating portion 8.

Main Actions and Effects of the Present Embodiment

The measurement device 1 includes the sensing portion 3, the measuring portion 5, and the irradiating portion 8. The sensing portion 3 contains at least the fluorescent material that ceases to emit fluorescent light when the neutron beam acts on it. In a case where the sensing portion 3 is irradiated by the neutron beam, the neutron beam acts on at least one portion of the fluorescent material. Fluorescent light stops being emitted from the at least one portion of the fluorescent material on which the neutron beam has acted. In this case, the intensity of the fluorescent light that is emitted from the fluorescent material as a whole decreases. Further, the amount of the decrease in the intensity of the fluorescent light varies in accordance with the neutron fluence of the neutron beam with which the sensing portion 3 is irradiated. Therefore, based on the amount of the decrease in the intensity of the fluorescent light, the measuring portion 5 can measure the neutron fluence of the neutron beam with which the sensing portion 3 is irradiated.

The measurement device 1 measures the neutron fluence based on the change in the fluorescent property of the fluorescent material that is due to the action of the neutron beam on the fluorescent material of the sensing portion 3. Therefore, as long as the sensing portion 3 contains the fluorescent material that is necessary for measuring the neutron fluence, no material other than the fluorescent material is required. The measurement device 1 is therefore able to inhibit any worsening of the transparency of the sensing portion 3 that would be due to a material contained in the sensing portion 3. This enables the measurement device 1 to measure the neutron fluence with high sensitivity.

The sensing portion 3 contains, as the fluorescent material, a material that contains lithium (Li), boron (B), and gadolinium (Gd), which are elements having large neutron capture cross sections. Irradiating the fluorescent material with a neutron beam destroys these elements, causing the fluorescent material to cease emitting fluorescent light. In other words, the change in the fluorescent property of the fluorescent material in response to the irradiating by the neutron beam is greater than it would be in a material that does not contain these elements. Accordingly, including the material that contains these elements as the fluorescent material in the sensing portion 3 enables the measurement device 1 to measure the neutron fluence with high sensitivity.

By subtracting the intensity of the fluorescent light after the neutron beam irradiation (Step S21) from the intensity of the fluorescent light before the neutron beam irradiation (Step 17), the measuring device 6 computes the amount of the decrease (Step S23). Based on the computed amount of the decrease, the measuring device 6 specifies the neutron fluence of the neutron beam that irradiated the sensing portion 3 (Step S25). In this case, using the intensity of the fluorescent light when the sensing portion 3 has not been irradiated by the neutron beam as a standard, the measurement device 1 is able to compute the amount of the decrease based on the intensity of the fluorescent light when the sensing portion 3 has been irradiated by the neutron beam. Accordingly, because the amount of the decrease in the intensity of the fluorescent light that accompanies the irradiating by the neutron beam can be specified accurately, the measurement device 1 is able to measure the neutron fluence with high precision.

The measurement device 1 includes the irradiating portion 8, which outputs the excitation light to the sensing portion 3. Being irradiated by an excitation source causes the fluorescent material to emit fluorescent light at an intensity that is proportional to the intensity of the excitation light. For every intensity level of the reflected light, which is the reflected excitation light, the relationship between the amount of the decrease and the neutron fluence of the neutron beam that irradiates the sensing portion 3 is stored in the measuring device 6 in advance. The measuring device 6 takes the neutron fluence that corresponds to the intensity of the reflected light that was measured at Step S17 and the amount of the decrease that was computed at Step S25 and specifies it as the neutron fluence of the neutron beam that irradiated the sensing portion 3. In this case, the measurement device 1 is able to specify the amount of the decrease with high precision, regardless of the stability of the excitation light and the stability of the first transmitting portion 4 and the second transmitting portion 7.

The measurement device 1 takes the excitation light that is output from the irradiating portion 8 and transmits it to the sensing portion 3 through the second transmitting portion 7 and the first transmitting portion 4. The measurement device 1 is thus able to transmit the excitation light efficiently to the sensing portion 3, irradiating the fluorescent material and causing it to emit fluorescent light. The measurement device 1 then takes the fluorescent light that has been emitted from the fluorescent material of the sensing portion 3 and transmits it to the measuring device 6 through the first transmitting portion 4 and the second transmitting portion 7. The measurement device 1 is thus able to transmit the fluorescent light efficiently to the measuring device 6. This in turn makes it possible for the measurement device 1 to measure the neutron fluence with high sensitivity. Furthermore, because the measurement device 1 is able to prevent light other than the fluorescent light (outside light and the like) from entering the measuring device 6, it can inhibit light other than the fluorescent light from influencing the measure results. The measurement device 1 can therefore measure the neutron fluence with high sensitivity. Further, providing the first transmitting portion 4 makes it possible to physically separate the sensing portion 3 of the measurement probe 2 from the measuring portion 5. The neutron beam can therefore be inhibited from irradiating the measuring portion 5, making it possible to prevent the measuring portion 5 from malfunctioning due to irradiation by the neutron beam.

The angle θ that is formed between the extension direction and the direction extending along each one of the radiating portion 31A of the sensing portion 31, the radiating portion 32A of the sensing portion 32, the pair of the radiating portions 34B of the sensing portion 34, and the pair of the radiating portions 35B of the sensing portion 35 is congruent with the maximum light-receiving angle of the first transmitting portion 4. In this case, the measurement device 1 is able to cause the fluorescent light that has been emitted from the fluorescent material of the sensing portion 3 to enter the first transmitting portion 4 efficiently and be transmitted to the measuring portion 5. Therefore, the measurement device 1 is able to measure the neutron fluence with even greater precision.

The flat portion 31B of the sensing portion 31 and the flat portion 34C of the sensing portion 34 are orthogonal to the extension direction. In this case, the fluorescent light that has been emitted from the sensing portion 3 can be reflected efficiently by the flat portions 31B, 34C and returned to the first transmitting portion 4. In other words, the measurement device 1 is able to cause even more of the fluorescent light that has been emitted from the fluorescent material of the sensing portion 3 to enter the first transmitting portion 4 and be transmitted to the measuring portion 5. The excitation light that has entered the sensing portion 3 from the first transmitting portion 4 can also be reflected efficiently by the flat portions 31B, 34C. In this case, the intensity of the fluorescent light that is emitted from the fluorescent material increases in response to the excitation light. Accordingly, the measurement device 1 is able to measure the neutron fluence accurately with even greater sensitivity.

The spherical surface portion 32B of the sensing portion 32 is disposed along the surface of a virtual sphere having its center at the position 320, which is connected to the first transmitting portion 4. The curved portion 35C of the sensing portion 35 is disposed along the side face of a virtual cylinder whose central axis passes through the position 350, which is connected to the first transmitting portion 4. In these cases, the fluorescent light that has been emitted from the fluorescent material of the sensing portion 3 is reflected by the spherical surface portion 32B and the curved portion 35C and can be concentrated at the positions 320, 350, respectively. In other words, the measurement device 1 is able to cause even more of the fluorescent light that has been emitted from the fluorescent material of the sensing portion 3 to enter the first transmitting portion 4 and be transmitted to the measuring portion 5. Accordingly, the measurement device 1 is able to measure the neutron fluence accurately with even greater sensitivity.

The sensing portions 31, 32 have substantially conical shapes. The sensing portion 33 has a spherical shape. In these cases, because the surface area is greater than on the plate-shaped sensing portions 34 to 36, more of the neutron beam can be made to act on the fluorescent material. Accordingly, the measurement device 1 is able to increase the sensitivity of the neutron fluence measurement. In contrast, the sensing portions 34 to 36 have plate shapes. Therefore, the sensing portions 34 to 36 can be held in a more stable manner by bringing the main face portions 34A, 35A, 36A into contact with the affected area of the patient.

The measurement device 1 is preferably used in a case where the neutron fluence being measured is that of a neutron beam with which a patient is irradiated in neutron capture therapy. In this case, by measuring the neutron fluence of a neutron beam with which a patient is irradiated in neutron capture therapy, the measurement device 1 makes it possible to conduct the therapy by irradiating the patient with an appropriate amount of the neutron beam.

In a state in which the sensing portion 3 is being irradiated with the neutron beam, the measuring device 6 cyclically repeats the specifying of the neutron fluence. In this case, the measurement device 1 is able to measure, in real time, the neutron fluence of the neutron beam with which the sensing portion 3 is being irradiated. Therefore, in a case where the measurement device 1 is used in neutron capture therapy, for example, it is possible to measure the neutron fluence with which the patient is being irradiated while the therapy is being conducted, so the neutron fluence can be adjusted in accordance with the state of the affected area while the therapy is being conducted.

Modified Examples

The present disclosure is not limited to the embodiment described above, and various types of modifications can be made. In the embodiment that is described above, the object of measurement by the measurement device 1 is the neutron fluence. In contrast, for example, a material that stops emitting fluorescent light in response to irradiation by a radioactive beam that includes a neutron beam may also be used as the fluorescent material that is contained in the sensing portion 3. In this case, the measurement device 1 may measure the neutron fluence based on the same principle that is described above.

The measuring device 6 may also output the measured light intensity to an arithmetic unit (a PC or the like) that is not shown in the drawings. The arithmetic unit may also compute the amount of the decrease in the fluorescent light by subtracting the intensity of the fluorescent light that was measured at Step S21 from the intensity of the fluorescent light that the measuring device 6 measured at Step S17. Based on the computed amount of the decrease, the arithmetic unit may also specify the neutron fluence of the neutron beam with which the sensing portion 3 of the measurement probe 2 was irradiated.

Figure 12:
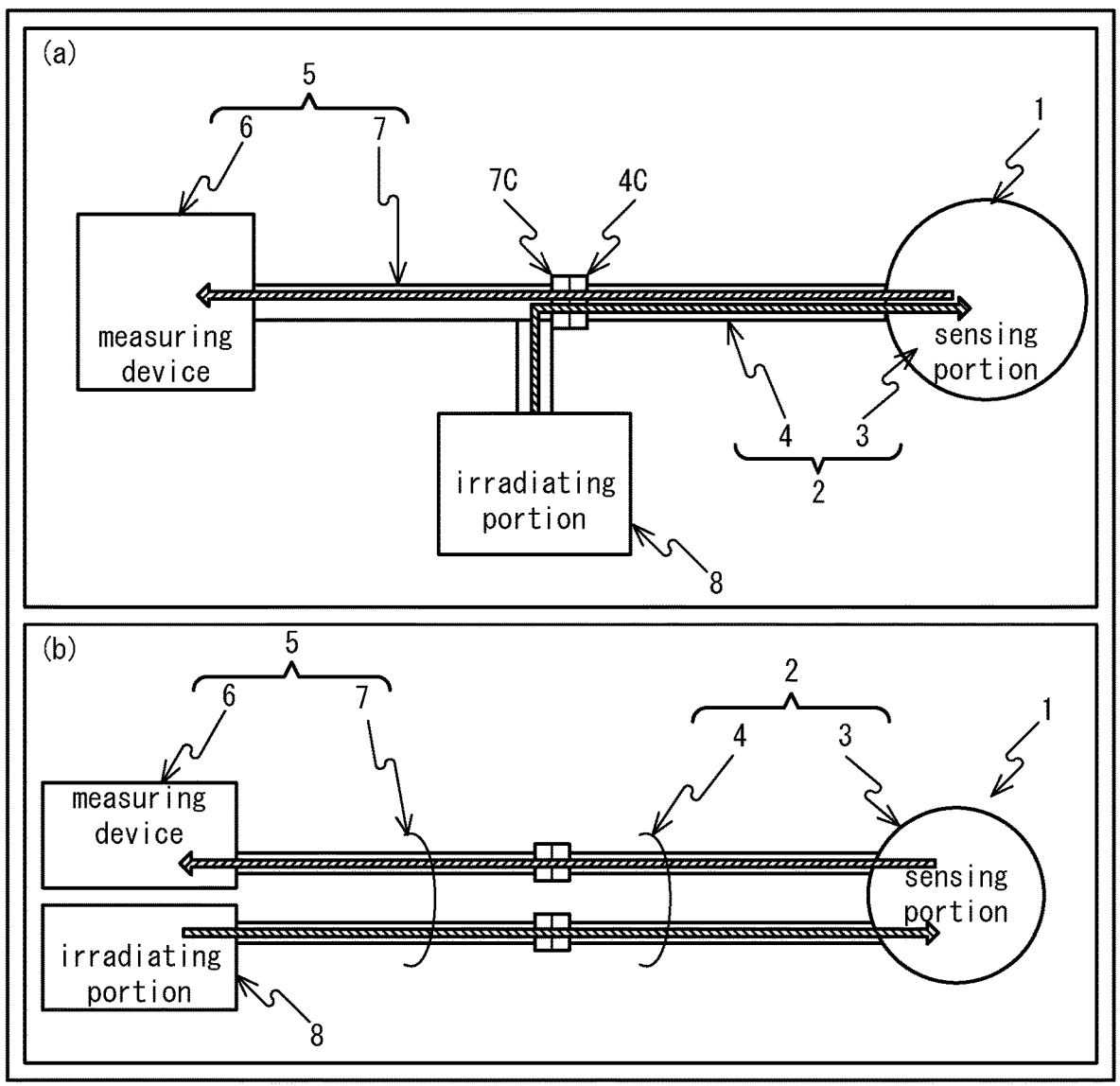
FIG. 12 is a figure showing an overview of the measurement device 1 in a modified example.

As shown in FIG. 12(a), the second transmitting portion 7 of the measuring portion 5 may also be divided into two parts at the joint 7C. The measuring device 6 may be connected to one end of one of the two parts of the divided second transmitting portion 7, and the irradiating portion 8 may be connected to one end of the other part. In this case, the dichroic mirror 71 shown in FIG. 1 becomes unnecessary. As shown in FIG. 12(b), two of each one of the first transmitting portion 4 and the second transmitting portion 7 may also be provided. One end of each one of the first transmitting portions 4 may be connected to the sensing portion 3. In contrast, one end of one of the second transmitting portions 7 may be connected to the measuring device 6, and one end of the other one of the second transmitting portions 7 may be connected to the irradiating portion 8. In other words, the excitation light that is output toward the sensing portion 3 from the irradiating portion 8 and the fluorescent light that is emitted from the fluorescent material of the sensing portion 3 may be transmitted through different transmitting portions.

The method for specifying the neutron fluence is not limited to the method in the embodiment that is described above. For example, a relational expression that indicates the relationship between the neutron fluence and the amount of the decrease in the fluorescent light may be derived in advance, and the derived expression may be stored in the measuring device 6. The measuring device 6 may then compute the neutron fluence by inputting the amount of the decrease that was computed at Step S23 to the relational expression that was derived in advance. As a form of calibration processing prior to starting the measurement, the measuring device 6 may also compute a correction count based on the intensity of the fluorescent light when the sensing portion 3 is being irradiated by a neutron beam with a specified neutron fluence. The measuring device 6 may compute the amount of the decrease in the fluorescent light by applying the correction count to the intensity of the fluorescent light that was measured during actual measurement, and then specify the neutron fluence based on the computed amount of the decrease.

The excitation light that is output from the irradiating portion 8 may also irradiate the sensing portion 3 directly, without passing through the first transmitting portion 4 and the second transmitting portion 7. The irradiating portion 8 may also output an electron beam instead of the excitation light. The fluorescent material may also emit fluorescent light when it is irradiated with an electron beam that has been output from the irradiating portion 8.

It is also acceptable for the measurement probe 2 not to include the first transmitting portion 4. The joint 7C of the second transmitting portion 7 of the measuring portion 5 may also be directly connected to the sensing portion 3. It is also acceptable for the measuring portion 5 not to include the second transmitting portion 7. In that case, the fluorescent light that is emitted from the fluorescent material of the sensing portion 3 may irradiate the area around the sensing portion 3. The measuring device 6 may also use a light receiving portion to receive a portion of the fluorescent light that irradiates the area around the sensing portion 3 and measure the intensity of the received fluorescent light.

It is also acceptable for the angle $\theta$ that is formed between the extension direction and the direction extending along each one of the radiating portion 31A of the sensing portion 31, the radiating portion 32A of the sensing portion 32, the pair of the radiating portions 34B of the sensing portion 34, and the pair of the radiating portions 35B of the sensing portion 35 not to be congruent with the maximum light-receiving angle of the first transmitting portion 4. For example, the angle $\theta$ may also be smaller than the maximum light-receiving angle of the first transmitting portion 4. The one of the transparent resin and the glass may also be laminated to the surfaces of the radiating portion 31A of the sensing portion 31, the radiating portion 32A of the sensing portion 32, the pair of the radiating portions 34B of the sensing portion 34, and the pair of the radiating portions 35B of the sensing portion 35. It is also acceptable for the fluorescent material not to be contained in the laminated portion. In that case, the angle $\theta$ that is formed between the extension direction and the surface of the portion of the sensing portion 3 that is laminated as described above may also be greater than the maximum light-receiving angle of the first transmitting portion 4. In other words, the angle that is formed between the extension direction and the region of the sensing portion 3 that contains the fluorescent material needs only to be substantially the same as the maximum light-receiving angle of the first transmitting portion 4.

The flat portion 31B of the sensing portion 31 and the flat portion 34C of the sensing portion 34 may also be inclined in relation to the extension direction. Raised and lowered areas may also be formed on the flat portions 31B, 34C. It is also acceptable for the center of the virtual sphere passing through the spherical surface portion 32B of the sensing portion 32 not to be coincident with the position 320. It is also acceptable for the central axis of the virtual cylinder passing through the curved portion 35C of the sensing portion 35 not to pass through the position 350. The respective centers may also be disposed on the first side of the positions 320, 350 in the extension direction and may also be disposed on the second side of the positions 320, 350 in the extension direction.

Naturally, the measurement device 1 can be used for purposes other than the measuring of the neutron fluence of a neutron beam in neutron capture therapy. The measurement device 1 may also store the fluorescent light intensities that have been measured within a specified time period. The measurement device 1 may also specify the neutron fluences for all of the stored fluorescent light intensities at once.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

The invention claimed is:

1. A measurement device, comprising:
a sensing portion containing at least a fluorescent material whose emitting of fluorescent light ceases due to an action of a neutron beam; and
a measuring portion measuring a neutron fluence of the neutron beam, with which the sensing portion is irradiated, based on an amount of decrease in the intensity of the fluorescent light emitted by the fluorescent material contained in the sensing portion when the neutron beam acts on at least a portion of the fluorescent material, the fluorescent light being emitted due to irradiation of the fluorescent material by an excitation source.

2. The measurement device according to claim 1, wherein the fluorescent material contains at least one of lithium, boron, cadmium, gadolinium, samarium, europium, and dysprosium.

3. The measurement device according to claim 1, wherein the measuring portion measures the neutron fluence based on a relationship between the intensity of the fluorescent light emitted from the fluorescent material before the sensing portion is irradiated by the neutron beam and the intensity of the fluorescent light emitted from the fluorescent material after the sensing portion is irradiated by the neutron beam.

4. The measurement device according to claim 1, further comprising:
an irradiating portion outputting the excitation source to the sensing portion,
wherein
the fluorescent material, due to being irradiated by the excitation source being output from the irradiating portion, emits the fluorescent light at an intensity corresponding to the intensity of the excitation source, and
the measuring portion measures the amount of the decrease in the intensity of the fluorescent light based on the intensity of the excitation source with which the sensing portion is irradiated.

5. The measurement device according to claim 1, further comprising:
a transmitting portion connected to the sensing portion and the measuring portion and transmitting to the measuring portion the fluorescent light emitted from the fluorescent material,
wherein
the measuring portion measures the neutron fluence based on the amount of the decrease in the intensity of the fluorescent light transmitted by the transmitting portion.

6. The measurement device according to claim 5, wherein
the sensing portion is shaped such that it includes a radiating portion extending radiating outward from a connecting portion with the transmitting portion, and
an angle of the radiating portion in relation to an extension direction along the transmitting portion from the connecting portion to the sensing portion is substantially the same as a maximum incidence angle of light capable of entering the transmitting portion.

7. The measurement device according to claim 1, wherein
the sensing portion is affixed to a patient during treatment by neutron capture therapy, and
the measuring portion measures the neutron fluence of the neutron beam with which the patient is irradiated in the neutron capture therapy.

8. The measurement device according to claim 1, wherein
the measuring portion repeatedly measures the neutron fluence in a state in which the sensing portion is being irradiated by the neutron beam.

9. A measurement probe used in a measurement device configured to measure a neutron fluence of a neutron beam, comprising:
a sensing portion containing at least a fluorescent material whose emitting of fluorescent light ceases due to an action of the neutron beam; and
a transmitting portion connected to the sensing portion and configured to transmit the fluorescent light being emitted due to irradiation of the fluorescent material by an excitation source.

10. The measurement probe according to claim 9, wherein the fluorescent material contains at least one of lithium, boron, cadmium, gadolinium, samarium, europium, and dysprosium.

11. The measurement probe according to claim 9, wherein
the sensing portion is shaped such that it includes a radiating portion extending radiating outward from a connecting portion with the transmitting portion, and
an angle of the radiating portion in relation to an extension direction along the transmitting portion from the connecting portion to the sensing portion is substantially the same as a maximum incidence angle of light capable of entering the transmitting portion.

* * * * *